US012123144B2

(12) United States Patent
Leggett et al.

(10) Patent No.: US 12,123,144 B2
(45) Date of Patent: Oct. 22, 2024

(54) ANTIMICROBIAL BIODEGRADABLE COMPOSITIONS FOR FOOD CONTACT ARTICLES

(71) Applicant: Danimer IPCo, LLC, Bainbridge, GA (US)

(72) Inventors: Carol G. Leggett, Whigham, GA (US); Phillip Van Trump, Decatur, GA (US); Thomas K. Leggett, III, Lexington, KY (US); Russell Mullins, Lagrange, GA (US)

(73) Assignee: Danimer IPCo, LLC, Bainbridge, GA (US)

( * ) Notice: Subject to any disclaimer, the term of this patent is extended or adjusted under 35 U.S.C. 154(b) by 0 days.

(21) Appl. No.: 17/198,793

(22) Filed: Mar. 11, 2021

(65) Prior Publication Data

US 2022/0056643 A1    Feb. 24, 2022

Related U.S. Application Data

(60) Provisional application No. 63/068,401, filed on Aug. 21, 2020.

(51) Int. Cl.
| | |
|---|---|
| *D21H 25/02* | (2006.01) |
| *B65D 65/46* | (2006.01) |
| *B65D 81/24* | (2006.01) |
| *B65D 81/28* | (2006.01) |
| *D21H 19/28* | (2006.01) |
| *D21H 23/50* | (2006.01) |

(52) U.S. Cl.
CPC .......... *D21H 25/02* (2013.01); *B65D 65/466* (2013.01); *B65D 81/24* (2013.01); *B65D 81/28* (2013.01); *D21H 5/0047* (2013.01); *D21H 19/28* (2013.01); *B32B 2307/7145* (2013.01); *B32B 2307/7163* (2013.01); *B32B 2307/764* (2013.01); *B32B 2439/70* (2013.01); *Y10T 428/13* (2015.01); *Y10T 428/1303* (2015.01); *Y10T 428/1307* (2015.01)

(58) Field of Classification Search
CPC .... B32B 2307/7145; B32B 2307/7163; B32B 2307/764; B32B 2439/70
USPC .............................................. 428/34.1–36.92
See application file for complete search history.

(56) References Cited

U.S. PATENT DOCUMENTS

| | | | | |
|---|---|---|---|---|
| 5,451,456 | A | * | 9/1995 | Marchessault ......... D21H 17/53 |
| | | | | 106/203.3 |
| 5,958,480 | A | * | 9/1999 | Eggink ................... C12P 7/625 |
| | | | | 426/90 |
| 8,828,516 | B2 | | 9/2014 | Durdag et al. |
| 2003/0157268 | A1 | * | 8/2003 | Gutowski ............ B27K 5/0055 |
| | | | | 427/532 |
| 2003/0217648 | A1 | * | 11/2003 | Noda ...................... C08L 67/04 |
| | | | | 99/485 |
| 2005/0175748 | A1 | * | 8/2005 | Thijssen ................ A01N 63/50 |
| | | | | 426/326 |
| 2008/0142023 | A1 | | 6/2008 | Schmid et al. |
| 2008/0169217 | A1 | * | 7/2008 | Bonneau ................ B65D 51/24 |
| | | | | 206/524.6 |
| 2008/0220036 | A1 | * | 9/2008 | Miltz .................... C08K 5/0058 |
| | | | | 424/409 |
| 2010/0178268 | A1 | * | 7/2010 | Bukshpan .............. A01N 25/34 |
| | | | | 424/78.08 |
| 2013/0295315 | A1 | * | 11/2013 | Durdag ..................... B32B 9/02 |
| | | | | 428/76 |
| 2018/0168157 | A1 | * | 6/2018 | De Meyer .............. A01N 59/02 |
| 2019/0351661 | A1 | * | 11/2019 | Romano ................. B32B 27/36 |
| 2020/0048493 | A1 | * | 2/2020 | Grubbs, III .............. C09D 5/14 |
| 2020/0114625 | A1 | * | 4/2020 | Van Trump ............ A47G 19/22 |
| 2020/0269557 | A1 | * | 8/2020 | Gallego Castro ...... B65D 65/40 |
| 2020/0354533 | A1 | * | 11/2020 | Tuszynski ............... A61L 27/54 |
| 2022/0195248 | A1 | * | 6/2022 | Lagaron Cabello . B65D 65/466 |

FOREIGN PATENT DOCUMENTS

| | | | | |
|---|---|---|---|---|
| CN | 107573530 | A | | 1/2018 |
| CN | 109566956 | A | | 4/2019 |
| CN | 109845761 | A | | 6/2019 |
| CN | 110358183 | A | | 10/2019 |
| EP | 374823 | A | * | 6/1990 ............. A01N 63/02 |
| EP | 0427912 | A1 | * | 5/1991 ............. A01N 63/02 |
| EP | 0466244 | | * | 1/1992 ............... A23B 4/22 |
| EP | 0466244 | A1 | | 1/1992 |
| EP | 0384319 | B1 | * | 4/1999 |
| EP | 2591682 | A1 | | 5/2013 |
| JP | 2011012221 | A | * | 1/2011 |
| WO | WO-2004056214 | A2 | * | 7/2004 ............. A01N 25/34 |
| WO | WO-2014060754 | | * | 4/2014 ............. C08L 67/04 |
| WO | 2014060754 | A3 | | 7/2014 |

(Continued)

OTHER PUBLICATIONS

E.R. Ekawati and W. Darmanto, 2019, IOP Conf. Ser.: Earth Environ. Sci. 217 012023 doi:10.1088/1755-1315/217/1/012023 (Year: 2019).*

Correa, Juan Pablo, et al., Improving ham shelf life with a polyhydroxybutyrate/polycaprolactone biodegradable film activated with nisin, Food Packaging and Shelf Life, vol. 11, Mar. 1, 2017, pp. 31-39.

(Continued)

*Primary Examiner* — Michael C Romanowski

(74) *Attorney, Agent, or Firm* — Luedeka Neely, P.C.

(57) ABSTRACT

The present disclosure provides a food contact article. According to one embodiment, the food contact article includes at least one food contact surface. This at least one food contact surface is made up of at least 50 weight percent of at least one biodegradable polymer, such as polyhydroxyalkanoates, and from about 0.1 weight percent to about 1.0 weight percent of at least one antimicrobial agent.

11 Claims, No Drawings

(56) References Cited

FOREIGN PATENT DOCUMENTS

| WO | 2015079419 A1 | 6/2015 | | |
|---|---|---|---|---|
| WO | WO-2015107089 A1 | * | 7/2015 | ............ A01N 25/10 |
| WO | WO-2018106191 A1 | * | 6/2018 | ............ B65D 65/46 |
| WO | 2020141242 A1 | 7/2020 | | |

OTHER PUBLICATIONS

Huang, Tianqi, et al., Polymeric Antimicrobial Food Packaging and Its Applications, Polymers, vol. 11, No. 3, Mar. 25, 2019, p. 560.
International Search Report and Written Opinion for PCT/US2021/021894, date of mailing Jun. 23, 2021, 17 pages.
Koller, Martin, Poly(hydroxyalkanoates) for Food Packaging: Application and Attempts towards Implementation, Applied Food Biotechnology, Dec. 17, 2014.
Munoz-Bonilla, Alexandra, et al., Bio-Based Polymers with Antimicrobial Properties towards Sustainable Development, Materials, vol. 12, No. 4, Feb. 20, 2019, p. 641.

\* cited by examiner ized as an antimicrobial agent. As used herein, the term "compostable" refers to a plastic or polymeric material that will undergo biodegradation in a composting environment such that the material is not visually distinguishable and breaks down into carbon dioxide, water, inorganic compounds, and biomass at a rate consistent with known compostable materials (as determined by ASTM D6400 or ASTM D6868).

ANTIMICROBIAL BIODEGRADABLE COMPOSITIONS FOR FOOD CONTACT ARTICLES

CROSS-REFERENCE TO RELATED APPLICATIONS

This application claims the benefit of the earlier filing date of U.S. provisional patent application 63/068,401, filed Aug. 21, 2020.

FIELD

This disclosure relates to biodegradable polymeric compositions. More particularly, this disclosure relates to polymeric compositions for food contact applications which are biodegradable and which also have antimicrobial properties.

BACKGROUND

Food borne illnesses are transmitted most commonly via the oral route. Therefore, decreasing the number of bacteria that are ingested is paramount to reducing gastrointestinal bacterial infections. In this regard, food containers can act as carrier materials in spreading bacteria and other pathogens from food handlers or can also serve as incubators in encouraging bacterial growth on warm food.

Thus, for improved food safety, it would be desirable to provide food containers that are capable of killing, or at least inhibiting the growth of, bacteria or other pathogens that may be introduced into the container at the time of service. Further, it would be particularly desirable to provide such a food container which is made from materials which are biodegradable and/or compostable.

SUMMARY OF THE INVENTION

In a first aspect, the present disclosure provides a food contact article. According to one embodiment, the food contact article includes at least one food contact surface. This at least one food contact surface is made up of at least 50 weight percent of at least one biodegradable polymer and from about 0.1 weight percent to about 1.0 weight percent of at least one antimicrobial agent.

In some embodiments, the food contact article is preferably a food container, a cup, an eating utensil, or a food packaging film.

According to certain embodiments, the food contact article is preferably made up of a biodegradable substrate having a coating formed thereon. This coating makes up the food contact surface and is preferably made up of at least 50 weight percent of the at least one biodegradable polymer and from about 0.1 weight percent to about 1.0 weight percent of at least one antimicrobial agent. More preferably, the biodegradable substrate is made up of paperboard.

In certain embodiments, the food contact surface is preferably made up of at least 75 weight percent of the at least one biodegradable polymer and more preferably from about 80 to about 99.9 weight percent of the at least one biodegradable polymer.

In some instances, the antimicrobial agent is preferably selected from the group consisting of anti-bacterial agents, anti-fungal agents, anti-parasitic agents, anti-algal agents, anti-prion agents, and combinations thereof.

In certain preferred embodiments, the antimicrobial agent is made up of lysozyme in an amount from about 0.1 to about 1.0 weight percent of the food contact article. Further, in certain embodiments, the food contact article also includes a second antimicrobial agent selected from the group consisting of anti-bacterial agents, anti-fungal agents, anti-parasitic agents, anti-algal agents, anti-prion agents, and combinations thereof.

In accordance with certain embodiments, the antimicrobial agent is preferably applied as a spray on the at least one food contact surface. In other embodiments, the antimicrobial agent may be applied as a coating. In still other embodiments, the antimicrobial agent may be applied by dipping the food contact article into a mixture of the antimicrobial agent and allowing the antimicrobial agent to be absorbed by the food contact surface.

In certain embodiments, the at least one biodegradable polymer is preferably selected from the group consisting of polyhydroxyalkanoates, poly(butylene succinate), poly(butylene succinate-co-adipate), poly(butylene adipate-co-terephthalate), poly(caprolactone), poly(lactic acid), cellulose esters, thermoplastic starch, and mixtures thereof. More preferably, the at least one biodegradable polymer comprises polyhydroxyalkanoates.

According to certain embodiments, the polyhydroxyalkanoates are preferably made up of a copolymer made up of from about 75 to about 99.9 mole percent monomer residues of 3-hydroxybutyrate and from about 0.1 to about 25 mole percent monomer residues of a second hydroxyalkanoate having from 5 to 12 carbon atoms.

In certain other embodiments, the polyhydroxyalkanoates are preferably made up of a terpolymer made up from about 75 to about 99.9 mole percent monomer residues of 3-hydroxybutyrate and from about 0.1 to about 25 mole percent monomer residues of 3-hydroxyhexanoate, and from about 0.1 to about 25 mole percent monomer residues of a third hydroxyalkanoate having from 5 to 12 carbon atoms.

In some instances, the polyhydroxyalkanoates preferably have an initial weight average molecular weight from about 50,000 to about 4,000,000 daltons, more preferably from about 100,000 to about 3,000,000 daltons, and most preferably from about 100,000 to about 2,000,000 daltons.

DETAILED DESCRIPTION

In one aspect, the present disclosure provides a food contact article. This food contact article includes at least one food contact surface. In many instances, the article my include a plurality of food contact surfaces. In certain embodiments, for example, the food contact article may take the form of a food container, a cup, an eating utensil, or a food packaging film.

In some instances, the food contact article is made up of a biodegradable substrate having a coating formed thereon. In such instances, the coating serves as the food contact surface. Preferably, this biodegradable substrate is made up of paperboard. Alternatively, however, this biodegradable substrate may be made up of film, sheet, cardboard, or paper.

According to the present disclosure, the food contact article is preferably biodegradable and/or compostable. More particularly the food contact article is both biodegradable and compostable.

As used herein, the term "biodegradable" refers to a plastic or polymeric material that will undergo biodegradation by living organisms (microbes) in anaerobic and aerobic environments (as determined by ASTM D5511), in soil environments (as determined by ASTM 5988), in freshwater environments (as determined by ASTM D5271 (EN 29408)), or in marine environments (as determined by ASTM D6691). The biodegradability of biodegradable plastics can also be determined using ASTM D6868 and European EN 13432.

As used herein, the term "compostable" refers to a plastic or polymeric material which may be either industrially or home composed in accordance with ASTM D6400.

In general, the food contact surface is made up of polyhydroxyalkanoates, as well as at least one antimicrobial agent.

In general, the least one food contact surface is made up of at least 50 weight percent of at least one biodegradable polymer. Preferably, the least one food contact surface is made up of at least 75 weight percent of the at least one biodegradable polymer. More preferably, the least one food contact surface is made up of at least 80 weight percent polyhydroxyalkanoates, and even more preferably from about 85 to about 99.9 weight percent of the at least one biodegradable polymer.

In certain embodiments, the at least one biodegradable polymer is preferably selected from the group consisting of polyhydroxyalkanoates, poly(butylene succinate), poly(butylene succinate-co-adipate), poly(butylene adipate-co-terephthalate, poly(caprolactone), poly(lactic acid), cellulose esters, thermoplastic starch, and mixtures thereof.

More preferably, the at least one biodegradable polymer comprises polyhydroxyalkanoates, and optionally additional biodegradable polymers as well. In some instances, the polyhydroxyalkanoates of the food contact surface may be made up of homopolymers, such as polyhydroxybutyrate. More typically however, the polyhydroxyalkanoates of the food contact surface are copolymers or even terpolymers formed from differing hydroxyalkanoates monomers.

For instance, in some embodiments, the polyhydroxyalkanoates are made up of a copolymer made up of from about 75 to about 99.9 mole percent monomer residues of 3-hydroxybutyrate and from about 0.1 to about 25 mole percent monomer residues of a second hydroxyalkanoate having from 5 to 12 carbon atoms. More preferably, the second hydroxyalkanoate is 3-hydroxyhexanoate.

In other embodiments, the polyhydroxyalkanoates are preferably made up of a terpolymer made up from about 75 to about 99.9 mole percent monomer residues of 3-hydroxybutyrate and from about 0.1 to about 25 mole percent monomer residues of 3-hydroxyhexanoate, and from about 0.1 to about 25 mole percent monomer residues of a third 3-hydroxyalkanoate having from 5 to 12 carbon atoms.

In general, the polyhydroxyalkanoates used in the food contact surface have an initial weight average molecular weight from about 50,000 to about 4,000,000 daltons. More preferably, the polyhydroxyalkanoates used in the food contact surface have an initial weight average molecular weight from about 100,000 to about 3,000,000 daltons, and most preferably from about 100,000 to about 2,000,000 daltons.

As noted above, the food contact surface includes at least one antimicrobial agent. For instance, the food contact surface may include at least one antimicrobial agent selected from the group consisting of anti-bacterial agents, anti-fungal agents, anti-parasitic agents, anti-algal agents, anti-prion agents, and combinations thereof.

Examples of suitable anti-bacterial agents which may be included in the food contact surface include zinc pyrithione, silver-based compounds, quaternary ammonia compounds, ethylenediaminetetraacetic acid (EDTA), and lysozyme.

Examples of suitable anti-fungal agents which may be included in the food contact surface include isothiazolinones and thiabendazole, *Lactobacilli* suspensions with or without chitosan, salicylic acid solutions, and natamycin.

Examples of suitable anti-parasitic agents which may be included in the food contact surface include atovaquone, pyrethroids, silver nanoparticles, permethrin, S-bioallethrin, piperonyl butoxide permethrin, pyriproxyfen, benzyl benzoate, flufenoxuron, and abamectin.

Examples of suitable anti-algal agents which may be included in the food contact surface include some biochemical products made by *Streptomycetes* sp. or phosphorus-deoxidised copper (Cu-DHP). Examples of suitable anti-prion agents which may be included in the food contact surface include pentosanpolysulfate, suramin, amphotericin B, congo red, dendritic polyamines, bis-acridine, polyphenol, phenothiazine, anti-histamine, statins, and quinacrine.

Preferably, the food contact surface includes at least an antibacterial agent. A particularly preferred antimicrobial agent is made up of lysozyme in an amount from about 0.1% to about 1.0% weight percent of the food contact article.

Lysozyme is an enzyme which is produced by animals and which exhibits antibacterial activity. Specifically, lysozyme catalyzes hydrolysis reactions which degrade the cell walls of gram-positive bacteria, eventually leading to lysis of the bacteria.

Given the ability of lysozyme to catalyze decomposition reactions by hydrolysis, it would have conventionally been expected that the use lyzsozyme would been incompatible with biodegradable polymers such as polyhydroxyalkanoates. Surprisingly, however, the present inventors have observed that the inclusion of lysozyme with polyhydroxyalkanoates does not lead to significant degradation of the polyhydroxyalkanoates.

In some embodiments, the food contact surface may include two or more antimicrobial agents used in combination. For instance, the food contact surface may include the lysozyme discussed above, together with a second antimicrobial agent selected from the group consisting of anti-bacterial agents, anti-fungal agents, anti-parasitic agents, anti-algal agents, anti-prion agents, and combinations thereof.

In accordance with certain embodiments, the antimicrobial agent is preferably applied as a spray on the at least one food contact surface. In other embodiments, the antimicrobial agent may be applied by aqueous coating, rotogravure, anilox, or formulative molding. In additional embodiments, the antimicrobial agent may be applied by dipping the food contact article into a bath of antimicrobial agent, so that agent is absorbed onto the food contact surface. In still other embodiments, the antimicrobial agent may be mixed with the polyhydroxyalkanoates prior to forming the food contact surface.

In some embodiments the food contact surface may also include other components in addition to the biodegradable polymer and the antimicrobial agent or agents. For instance, the food contact surface may also include a nucleating agent, a plasticizer, filler, and/or an impact modifier.

Suitable nucleating agents for use in the food contact surface may for example be selected from the group consisting of erythritols, pentaerythritol, dipentaerythritols, artificial sweeteners, stearates, sorbitols, mannitols, inositols, polyester waxes, nanoclays, behenamide, erucamide, stearamide, oleamide, polyhydroxybutyrate, and mixtures thereof.

Suitable plasticizers for use in the food contact surface may for example be selected from the group consisting of sebacates, citrates, fatty esters of adipic, succinic, and glucaric acids, lactates, alkyl diesters, citrates, alkyl methyl esters, dibenzoates, propylene carbonate, caprolactone diols having a number average molecular weight from 200-10,000 g/mol, poly(ethylene)glycols having a number average molecular weight of 400-10,000 g/mol, esters of vegetable oils, long chain alkyl acids, adipates, glycerol, isosorbide derivatives or mixtures thereof., HALLGREEN® IM-8830 ester, HALLGREEN® R-8010 ester, polyhydroxyalkanoate copolymers comprising at least 18 mole percent monomer residues of hydroxyalkanoates other than hydroxybutyrate, and mixtures thereof.

Suitable fillers for use in the food contact surface may for example be selected from the group consisting of calcium carbonate, talc, nano clays, nanocellulose, hemp fibers, kaolin, carbon black, wollastonite, glass fibers, carbon fibers, graphite fibers, mica, silica, dolomite, barium sulfate, magnetite, halloysite, zinc oxide, titanium dioxide, montmorillonite, feldspar, asbestos, boron, steel, carbon nanotubes, cellulose fibers, flax, cotton, starch, polysaccharides, aluminum hydroxide, magnesium hydroxide, chitin, and mixtures thereof.

Suitable impact modifiers for use in the food contact surface may for example be selected from the group consisting of organic peroxy acids, inorganic peroxy acids, isosorbide derivatives, or mixtures thereof.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A food contact article having at least one food contact surface, wherein the at least one food contact surface comprises at least 50 weight percent polyhydroxyalkanoates and from about 0.1 weight percent to about 1.0 weight percent lysozyme, wherein the lysozyme is absorbed onto the food contact surface so as to contact food.

2. The food contact article of claim 1, wherein the food contact article comprises a food container, a cup, an eating utensil, or a food packaging film.

3. The food contact article of claim 1, wherein the food contact article comprises a biodegradable substrate and the food contact surface comprises a coating formed on the substrate.

4. The food contact article of claim 3, wherein the biodegradable substrate comprises paperboard.

5. The food contact article of claim 1, wherein the food contact surface comprises from about 80 to about 99.9 weight percent of polyhydroxyalkanoates.

6. The food contact article of claim 1, further comprising a second antimicrobial agent selected from the group consisting of anti-bacterial agents, anti-fungal agents, anti-parasitic agents, anti-algal agents, anti-prion agents, and combinations thereof.

7. The food contact article of claim 1, wherein the lysozyme is applied as a spray on the at least one food contact surface.

8. The food contact article of claim 1, wherein the food contact surface further comprises at least one biodegradable polymer selected from the group consisting of poly(butylene succinate), poly(butylene succinate-co-adipate), poly(butylene adipate-co-terephthalate), poly(caprolactone), poly(lactic acid), cellulose esters, thermoplastic starch, and mixtures thereof.

9. The food contact article of claim 1, wherein the polyhydroxyalkanoates comprise a copolymer made up of from about 75 to about 99.9 mole percent monomer residues of 3-hydroxybutyrate and from about 0.1 to about 25 mole percent monomer residues of a second hydroxyalkanoate having from 5 to 12 carbon atoms.

10. The food contact article of claim 1, wherein the polyhydroxyalkanoates comprise a terpolymer made up from about 75 to about 99.9 mole percent monomer residues of 3-hydroxybutyrate and from about 0.1 to about 25 mole percent monomer residues of 3-hydroxyhexanoate, and from about 0.1 to about 25 mole percent monomer residues of a third hydroxyalkanoate having from 5 to 12 carbon atoms.

11. The food contact article of claim 1, wherein the polyhydroxyalkanoates have an initial weight average molecular weight from about 100,000 to about 3,000,000 daltons.

* * * * *